(12) United States Patent
Charles

(10) Patent No.: US 12,053,415 B2
(45) Date of Patent: Aug. 6, 2024

(54) ACUTE GLAUCOMA DEVICE

(71) Applicant: Alcon Inc., Fribourg (CH)

(72) Inventor: Steven T. Charles, Memphis, TN (US)

(73) Assignee: Alcon Inc., Fribourg (CH)

( * ) Notice: Subject to any disclaimer, the term of this patent is extended or adjusted under 35 U.S.C. 154(b) by 434 days.

(21) Appl. No.: 17/199,532

(22) Filed: Mar. 12, 2021

(65) Prior Publication Data

US 2021/0290436 A1   Sep. 23, 2021

Related U.S. Application Data

(60) Provisional application No. 62/990,722, filed on Mar. 17, 2020.

(51) Int. Cl.
| | |
|---|---|
| *A61F 9/007* | (2006.01) |
| *A61M 27/00* | (2006.01) |
| *A61F 9/00* | (2006.01) |
| *A61F 9/008* | (2006.01) |
| *A61M 39/24* | (2006.01) |

(52) U.S. Cl.
CPC ......... *A61F 9/00781* (2013.01); *A61M 27/00* (2013.01); *A61F 9/0017* (2013.01); *A61F 9/007* (2013.01); *A61F 9/00736* (2013.01); *A61F 2009/00891* (2013.01); *A61M 27/002* (2013.01); *A61M 27/006* (2013.01); *A61M 39/24* (2013.01); *A61M 2205/04* (2013.01); *A61M 2210/0612* (2013.01)

(58) Field of Classification Search
CPC ...... A61F 9/00781; A61F 9/0017; A61F 2/14; A61F 9/007; A61F 9/00736; A61F 2009/00891; A61M 2210/0612; A61M 27/002; A61M 27/00; A61M 2205/04; A61M 27/006; A61M 39/24
See application file for complete search history.

(56) References Cited

U.S. PATENT DOCUMENTS

| | | | |
|---|---|---|---|
| 7,846,134 B1 * | 12/2010 | Nadolski ............ | A61B 17/3421 604/164.11 |
| 2004/0254517 A1 * | 12/2004 | Quiroz-Mercado ........................ | A61F 9/00781 604/8 |
| 2010/0274259 A1 * | 10/2010 | Yaron ................. | A61M 27/002 604/8 |

(Continued)

*Primary Examiner* — Kai H Weng
(74) *Attorney, Agent, or Firm* — PATTERSON + SHERIDAN, LLP

(57) ABSTRACT

Embodiments disclosed herein provide devices, systems, and methods for reducing intraocular pressure. For example, the disclosed devices, systems, and methods are useful for reducing intraocular pressure resulting from conditions, such as acute glaucoma, on a short-term basis until a definitive surgical procedure is performed. More particularly, valved trocar cannula systems for reducing intraocular pressure resulting from conditions, such as acute glaucoma, pending surgical intervention in an operating room are disclosed. In practice, a trocar assembly is used to place a valved cannula assembly in a patient's eye, such as in the anterior chamber or pars plana, to reduce high intraocular pressure. The valved cannula is then left in the patient's eye for a period of time to continuously allow aqueous humor or liquid vitreous humor to flow therethrough, until the patient may be surgically treated in an operating room.

13 Claims, 5 Drawing Sheets

(56) References Cited

U.S. PATENT DOCUMENTS

| | | | |
|---|---|---|---|
| 2012/0172668 A1* | 7/2012 | Kerns | A61F 9/00736 |
| | | | 600/208 |
| 2012/0271272 A1* | 10/2012 | Hammack | A61M 5/486 |
| | | | 604/257 |
| 2016/0058615 A1* | 3/2016 | Camras | A61F 9/00781 |
| | | | 604/9 |
| 2019/0091012 A1* | 3/2019 | Kalina, Jr. | A61F 2/1664 |
| 2019/0374248 A1* | 12/2019 | Grueebler | A61B 17/00234 |

* cited by examiner

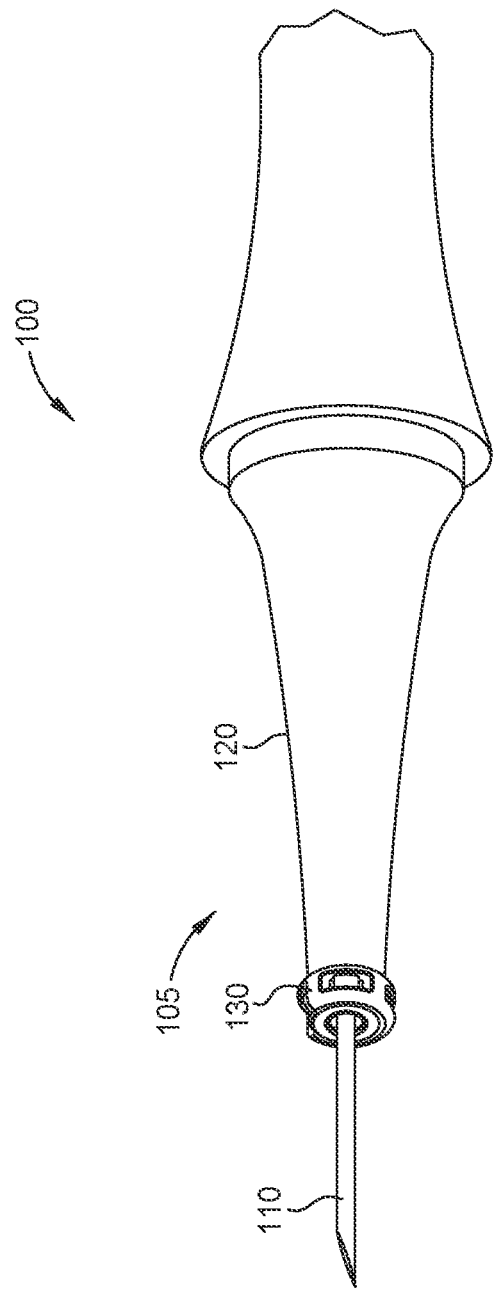
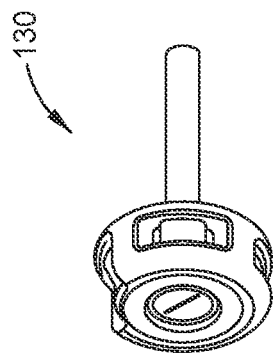
FIG. 1A
FIG. 1B

ACUTE GLAUCOMA DEVICE

TECHNICAL FIELD

The present disclosure relates generally to devices, systems, and methods for reducing intraocular pressure resulting from conditions, such as acute glaucoma. More particularly, the present disclosure relates to valved trocar cannula systems and methods of use thereof, which are useful to temporarily reduce intraocular pressure until a patient undergoes a definitive surgical procedure.

BACKGROUND

Glaucoma is a form of optic neuropathy in which the patient's optic nerve fibers are damaged by elevated intraocular pressure. In many cases, glaucoma is associated with an elevated intraocular pressure (IOP) that results when the aqueous humor, a clear liquid in the anterior chamber of the eye and vitreous cavity, cannot drain properly through the trabecular meshwork. The elevated intraocular pressure can damage the optic nerve fibers and may ultimately result in vision loss, if not treated quickly and effectively.

Conventionally, intraocular pressure has been reduced during standard glaucoma surgeries, which are major surgeries that are performed in an operating room and have a litany of potential complications. In more recent years, minimally invasive glaucoma surgeries (MIGs) have been used to implant micro-stents or other small devices from inside of the eye to reduce intraocular pressure. MIGs have fewer potential complications; however, MIGs must still be performed in an operating room and are generally intended for permanent placement of the micro-stent or other small device in the patient's eye. Moreover, MIGs generally do not adequately lower intraocular pressure for patients who have advanced glaucoma and require much greater lowering of their intraocular pressure. In addition to the aforementioned concerns, it is often true that a definitive surgical procedure cannot be performed immediately, often leaving the patient in severe pain and at risk for vision loss until the surgical procedure can be performed.

Therefore, there is a need for short-term management devices, systems, and methods for adequately reducing intraocular pressure.

BRIEF SUMMARY

The present disclosure relates generally to devices, systems, and methods for temporarily reducing intraocular pressure resulting from a condition, such as acute glaucoma, until the patient may be surgically treated in an operating room.

In one embodiment, a valved cannula assembly, which is useful to reduce intraocular pressure, is disclosed. The valved cannula assembly includes a cannula having a hollow rod portion, the hollow rod portion having a first opening and a second opening at opposite ends thereof and one or more openings along a length therebetween, a head portion, and a valved hub coupled to the head portion.

In another embodiment, a trocar cannula system, which is useful to reduce intraocular pressure, is disclosed. The trocar cannula system includes a trocar assembly and a valved cannula assembly detachably coupled to the trocar assembly. The trocar assembly includes a trocar blade and a trocar handle coupled to the trocar blade. The valved cannula assembly includes a cannula having a hollow rod portion, the hollow rod portion having a first opening and a second opening at opposite ends thereof and one or more openings along a length therebetween, a head portion, and a valved hub coupled to the head portion.

In yet another embodiment, a method of using a trocar cannula system to reduce intraocular pressure. The method includes inserting a valved cannula assembly through a trocar micro-incision a patient's eye wall, and leaving the valved cannula assembly disposed through the patient's eye wall to reduce the patient's intraocular pressure.

The following description and the related drawings set forth in detail certain illustrative features of one or more embodiments.

BRIEF DESCRIPTION OF THE DRAWINGS

The appended figures depict certain aspects of one or more disclosed embodiments and are therefore not to be considered limiting of the scope of this disclosure.

FIG. 1A illustrates a valved trocar cannula system, in accordance with certain embodiments of the present disclosure.

FIG. 1B illustrates an enlarged view of a valved cannula assembly of the valved trocar cannula system of FIG. 1A, in accordance with certain embodiments of the present disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Figure 2:
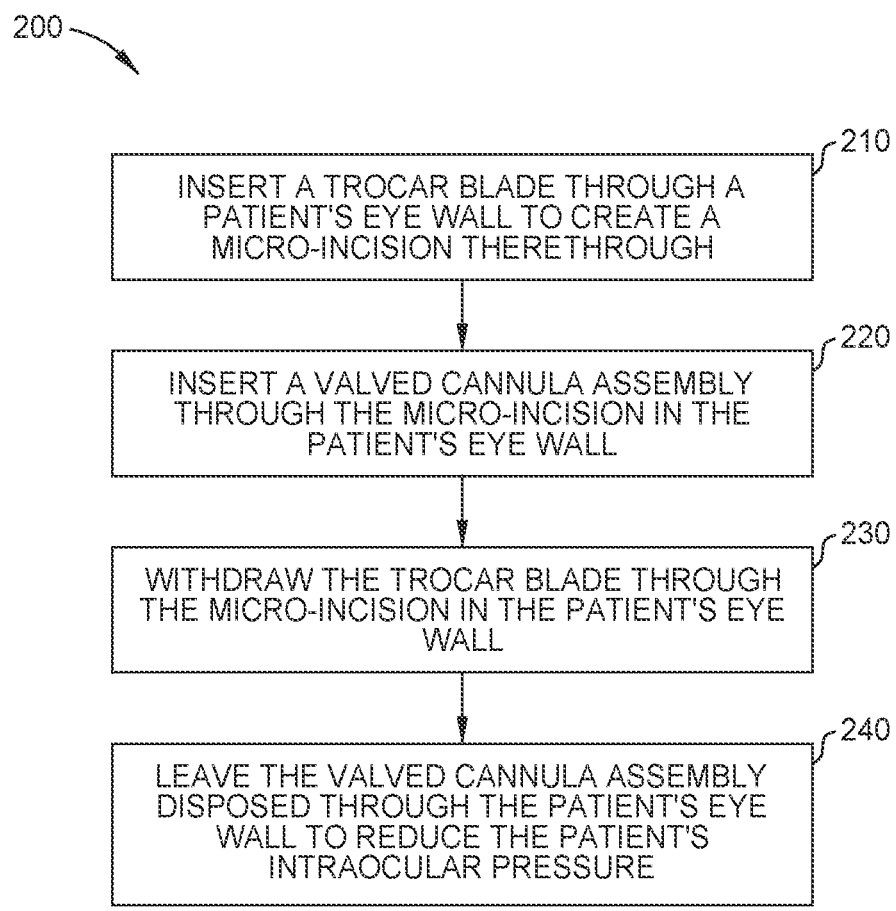
FIG. 2 is a flow diagram illustrating an example method of using a trocar cannula system to reduce intraocular pressure, in accordance with certain embodiments of the present disclosure.

Embodiments disclosed herein provide devices, systems, and methods for reducing intraocular pressure. For example, the disclosed devices, systems, and methods are useful for reducing intraocular pressure resulting from a condition, such as acute glaucoma on a short-term basis until a definitive surgical procedure is performed. More particularly, valved trocar cannula systems for reducing intraocular pressure resulting from conditions, such as acute glaucoma, pending surgical intervention in an operating room are disclosed. In practice, a trocar assembly is used to place a valved cannula assembly in a patient's eye, such as in the anterior chamber or the pars plana, to reduce high intraocular pressure. The valved cannula is then left in the patient's eye for a period of time to continuously allow aqueous humor or liquid vitreous humor to flow therethrough, until the patient may be surgically treated in an operating room.

As described above, existing methods for treating glaucoma and thus reducing intraocular pressure include surgical procedures that must be performed in an operating room. Oftentimes, the surgical procedures cannot be performed for several hours to a few days depending on surgeon and operating room availability. During the delay, the patient may experience severe pain and even vision loss. Accordingly, certain embodiments provide devices, systems, and methods for temporarily reducing intraocular pressure resulting from conditions, such as acute glaucoma, until the patient may be surgically treated in an operating room.

FIG. 1A illustrates a valved trocar cannula system 100. Trocar cannula systems, like the trocar cannula system 100, are useful for a variety of ophthalmological procedures since they facilitate insertion of an instrument through a micro-incision in the patient's eye wall and protect the incision sidewall from repeated contact when multiple instruments are placed therethrough.

As shown in FIG. 1A, the valved trocar cannula system 100 includes a trocar assembly 105 that is detachably coupled to a valved cannula assembly 130, which may be used to reduce intraocular pressure resulting from conditions, such as acute glaucoma. The trocar assembly 105 includes a trocar blade 110 and a trocar handle 120. The trocar handle 120 is used by a medical professional to guide and control the trocar blade 110 to the site of insertion. FIG. 1B illustrates an enlarged view of the valved cannula assembly 130. The valved cannula assembly 130 is configured to be detachably coupled to the trocar assembly 105, for example using a threaded connection or a snap connection mechanism. In operation, the trocar blade 110 is inserted through the eye wall to create a micro-incision (e.g., a hole) through the eye wall through which the valved cannula assembly 130 may be inserted and then remain disposed, for example, through various stages of a surgical procedure for the insertion of surgical instruments, or as contemplated by this disclosure, until the patient undergoes definitive glaucoma treatment surgery.

FIG. 2 is a flow diagram illustrating a method 200 of using a trocar cannula system, such as the valved trocar cannula system 100, to reduce intraocular pressure, in accordance with certain embodiments of the present disclosure. Method 200 is described below with reference to FIG. 3, which illustrates a cross-sectional view of a patient's eye 300 having a valved cannula assembly 330 disposed therein, in accordance with certain embodiments of the present disclosure.

The method 200 begins at operation 210 by inserting a trocar blade through a patient's eye wall 350 (including the sclera/cornea 352) to create a micro-incision through the patient's eye wall, such as in the anterior chamber or the pars plana, to reduce high intraocular pressure. At operation 220, a valved cannula assembly, which is detachably coupled to the trocar blade, is inserted through the micro-incision made by the trocar in the patient's eye wall 350. At operation 230, the trocar blade is withdrawn through the micro-incision in the patient's eye wall. And, at operation 240, the valved cannula assembly 330 is left disposed through the patient's eye wall 350 to reduce the patient's intraocular pressure by providing a channel through which aqueous humor may flow out to the external surface of the eye. In operation, when disposed through the patient's eye wall, the valved cannula assembly 330 provides a channel through which aqueous humor can continuously flow to the external side of the eye wall to reduce intraocular pressure for a period of time, such as up to three days.

The method 200 may be performed using any suitable valved trocar cannula system, including the embodiments of the valved trocar cannula systems described herein.

Figure 4A:
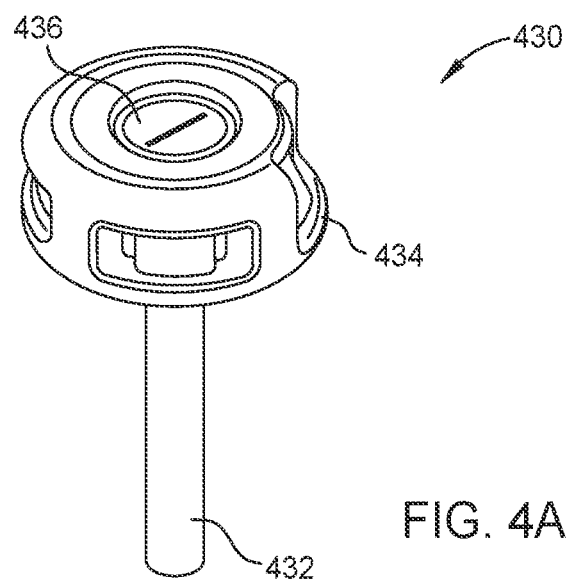
FIG. 4A illustrates a valved cannula assembly, in accordance with certain embodiments of the present disclosure.
Figure 4B:
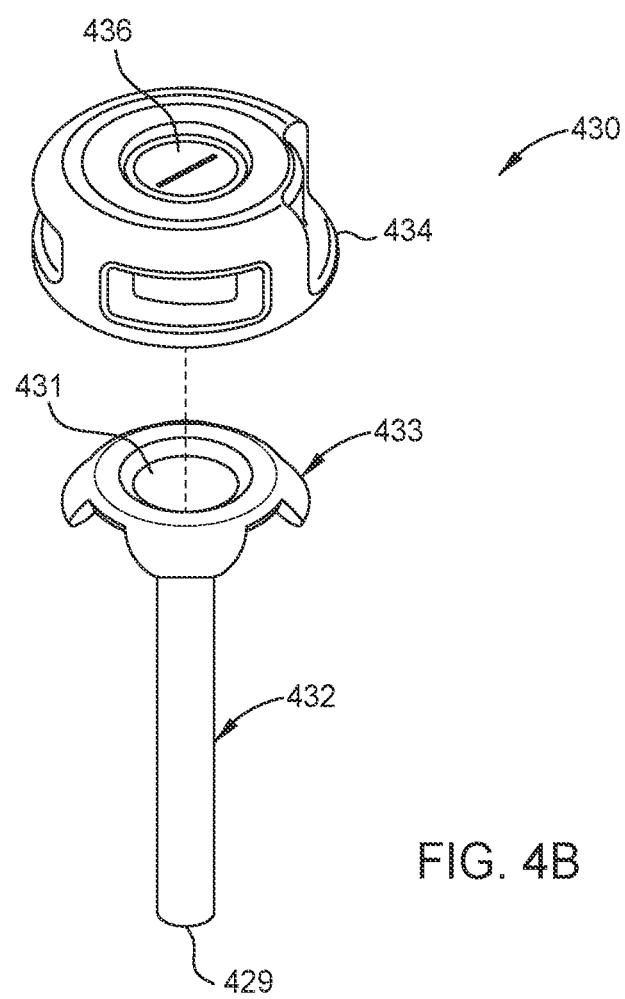
FIG. 4B illustrates an exploded view of the valved cannula assembly of FIG. 4A, in accordance with certain embodiments of the present disclosure.

FIG. 4A illustrates a schematic perspective view of a valved cannula assembly 430 and FIG. 4B illustrates an exploded schematic perspective view of the valved cannula assembly 430, in accordance with certain embodiments of the present disclosure. The valved cannula assembly 430 includes a hollow rod portion 432 and a head portion 433. The hollow rod portion 432 has openings 429, 431 at either end, which are connected by a hollow passageway. A valved hub 434 covers the head portion 433. The valved hub 434 is generally chamfered and has a valve 436 at a central portion thereof, which is aligned with the openings of the hollow rod portion 432, and through which the trocar blade may be withdrawn. Together, the hollow rod portion 432 and the head portion having the valved hub 434 form a working channel through which various instruments can be inserted to access the body part. In addition, as contemplated by the present disclosure, the valve 436 is configured to allow aqueous humor fluid to flow therethrough to the outside of the patient's eye wall to reduce intraocular pressure, while also acting as a seal to reduce the risk of intrusion of irritants, such as tear film, which is the mixture of substances secreted on the external ocular surface, that has been contaminated, for example, by bacteria. The valved hub 434 also provides a stopping mechanism to prevent the valved cannula assembly 430 from being wholly inserted all the way into the interior region of the eyeball.

The valve 436 is generally made of any suitable material, including silicone material, which is configured to prevent intraocular pressure from being too low as well as too high, for example to help maintain an intraocular pressure of between about 10 and about 25 millimeters of mercury (mmHg). When disposed through the patient's eye wall, as set forth above, the valved hub 434 is generally located on the external side of the patient's eye wall, and the hollow rod portion 432 extends into the interior region of the patient's eye. Accordingly, when the valved cannula assembly 430 is disposed in the patient's eye wall as disclosed herein, the valved cannula assembly 430 facilitates continuous flow of aqueous humor out of the interior region of the eye to reduce the patient's intraocular pressure.

Figure 5:
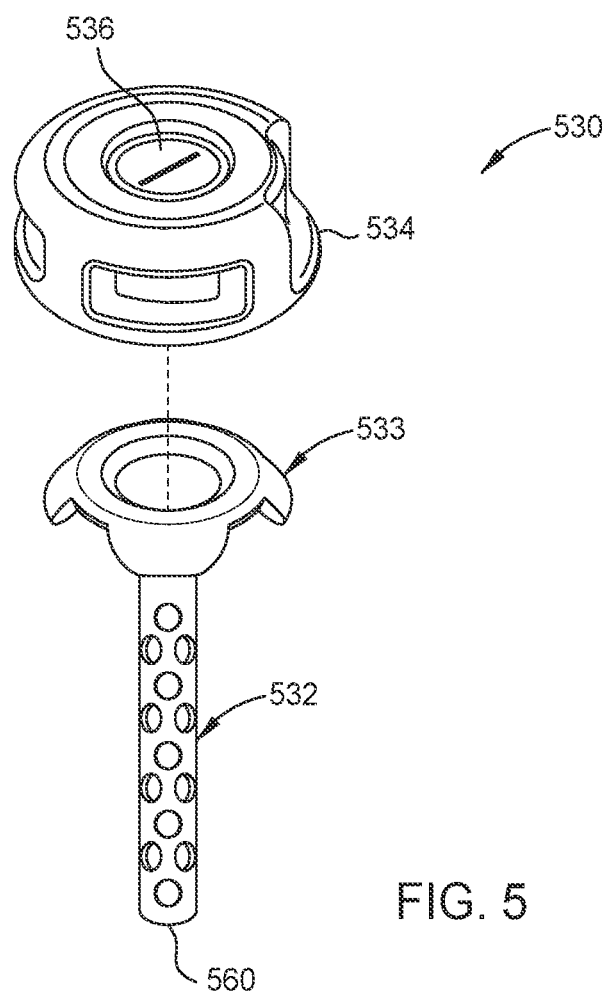
FIG. 5 illustrates an exploded view of a valved cannula assembly, in accordance with certain embodiments of the present disclosure.

FIG. 5 illustrates a schematic perspective view of a valved cannula assembly 530, in accordance with certain embodiments of the present disclosure. As shown in FIG. 5, as an example, the hollow rod portion 532 is fenestrated such that is has a plurality of openings 560 along the length thereof. As set forth above, the hollow rod portion 532 has openings at the ends thereof, which are connected by a hollow passageway there between. In some cases, vitreous humor, the gelatinous tissue that fills the eyeball behind the lens, may plug the openings at the ends of the hollow rod portion 532. The plurality of openings 560 along the length of the hollow rod portion 532 therefore allow for aqueous humor to continue to pass through the valved cannula assembly 530 to reduce intraocular pressure even when one of the openings is partially or fully blocked by vitreous humor.

Figure 3:
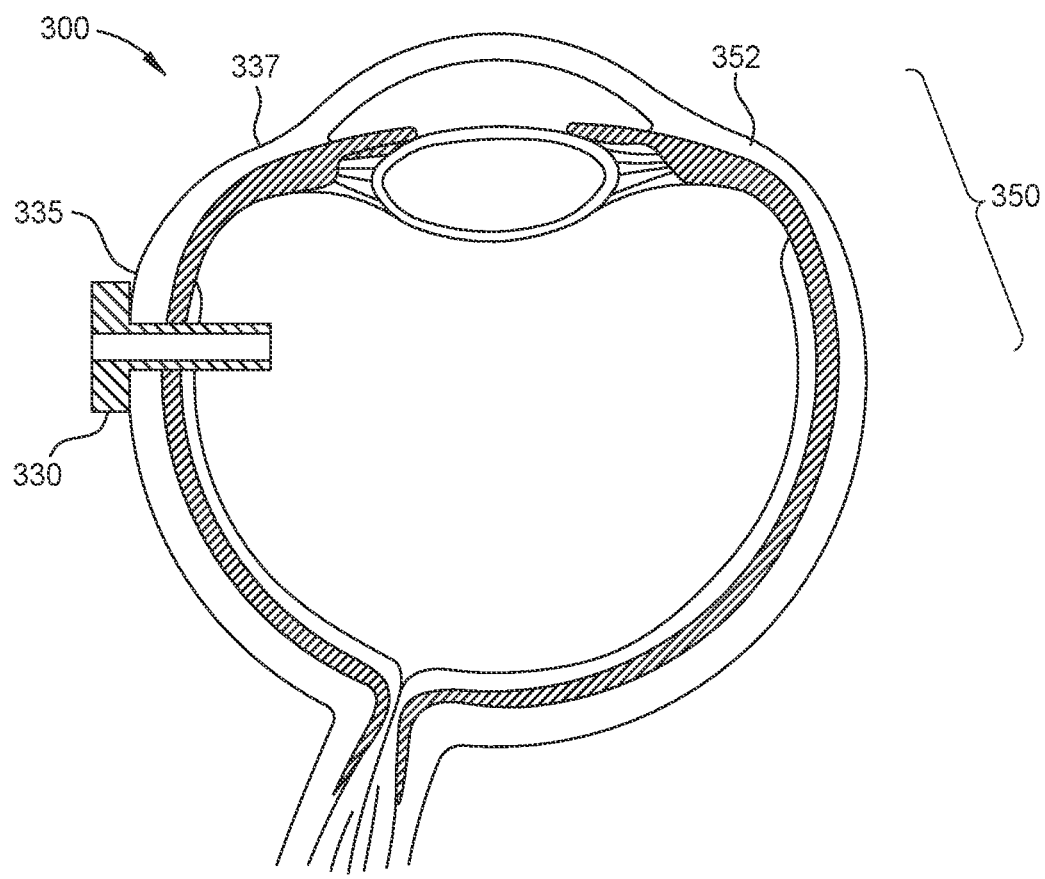
FIG. 3 illustrates a patient's eye having a valved cannula assembly disposed therein, in accordance with certain embodiments of the present disclosure.
Figure 6:
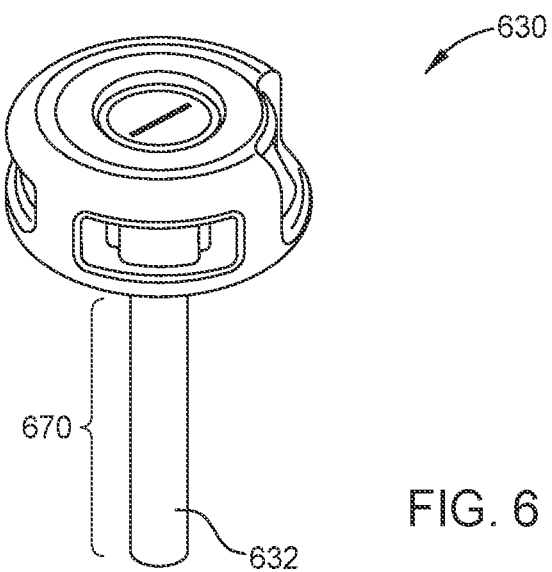
FIG. 6 illustrates a valved cannula assembly, in accordance with certain embodiments of the present disclosure.

FIG. 6 illustrates a schematic perspective view of a valved cannula assembly 630, in accordance with certain embodiments of the present disclosure. As set forth above, the valved cannula assembly 630 may be inserted through the patient's eye wall at the location of high intraocular pressure. For example, the valved cannula assembly 630 may be inserted through the pars plana 335, as shown in FIG. 3, or through the limbus 337 (also shown in FIG. 3). Conventionally, valved cannula assemblies used in other applications have been inserted through the eye wall at an angle thus requiring a longer length, such as greater than about 4 millimeters (mm). When inserted through the limbus to reduce intraocular pressure, however, the valved cannula assembly 630 may be inserted perpendicular to the eye wall and the length of the hollow rod portion 632 is therefore generally any suitable reduced length for traversing the eye wall perpendicularly. For example, the length 670 may be less than or equal to about 4 mm, such as less than or equal to about 2 mm. The reduced length of the hollow rod portion 632 beneficially reduces the risk of damaging the lens or iris.

While FIG. 5 shows the hollow rod portion 532 having a plurality of openings 560 and FIG. 6 shows a shorter hollow rod portion 632 without any openings, it is contemplated that the hollow rod portion 532, 632 may include any suitable number of openings of any suitable size and shape along the length thereof. The one or more openings may be evenly spaced apart or unevenly spaced along the length of the hollow rod portion 532, 632.

Accordingly, devices, systems, and methods are provided for temporarily reducing intraocular pressure resulting from conditions, such as acute glaucoma until the patient may be surgically treated in an operating room.

In effect, embodiments disclosed herein provide devices, systems, and methods, which lower very high intraocular pressure to at least a moderate intraocular pressure (between about 10 mmHg and about 20 mmHg) and prevent blindness while the patient awaits surgical intervention in an operating room. The disclosed devices, systems, and methods temporarily prevent hypotony, prevent excessively high pressure, and prevent ingress of contaminated tear film of the patient. Moreover, the disclosed methods are generally performed in the office setting to provide immediate lowering of the intraocular pressure and allow continuous slow leakage of the aqueous humor through the valve while the patient awaits definitive glaucoma surgery performed in an operating room. Disclosed embodiments are described in relation to lowering the intraocular pressure resulting from acute glaucoma, as an example; however, it is also contemplated that the disclosed embodiments are useful in different contexts and situations, such as for lowering the intraocular pressure resulting from other conditions or diseases.

Practically, the disclosed devices, systems, and methods provide short-term reduction of intraocular pressure, which provides the patient with immediate pain reduction, and reduced risk of vision loss, while awaiting a definitive surgical procedure, which may not occur until up to two to three days later, if for example, an acute glaucoma attack occurs in the middle of the night, over the weekend, or during a holiday.

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

What is claimed is:

1. A valved cannula assembly configured to reduce intraocular pressure, comprising:
    a cannula, comprising:
        a hollow rod portion, the hollow rod portion having a first opening and a second opening at opposite ends thereof and one or more openings along a length therebetween; and
        a head portion, comprising:
            a plurality of protrusions extending laterally outward from the head portion; and
    a valved hub, comprising:
        a sidewall having a plurality of apertures formed therein, the plurality of apertures configured to receive the plurality of protrusions to couple the valved hub to the head portion.

2. The valved cannula assembly of claim 1, wherein the hollow rod portion is fenestrated.

3. The valved cannula assembly of claim 1, wherein a length of the hollow rod portion is less than or equal to four millimeters.

4. The valved cannula assembly of claim 1, wherein a length of the hollow rod portion is less than or equal to two millimeters.

5. The valved cannula assembly of claim 1, wherein the valved hub comprises a valve, wherein the valve is aligned with the first opening and the second opening of the hollow rod portion.

6. The valved cannula assembly of claim 5, wherein the valve is configured to allow aqueous humor fluid to flow therethrough.

7. The valved cannula assembly of claim 1, wherein the valved hub comprises a material configured to help maintain an intraocular pressure of between about 10 and about 25 millimeters of mercury (mmHg).

8. A trocar cannula system configured to reduce intraocular pressure, comprising:
    a trocar assembly, comprising:
        a trocar blade; and
        a trocar handle coupled to the trocar blade; and
    a valved cannula assembly detachably coupled to the trocar assembly, comprising:
        a cannula, comprising:
            a hollow rod portion, the hollow rod portion having a first opening and a second opening at opposite ends thereof and one or more openings along a length therebetween; and
            a head portion, comprising:
                a plurality of protrusions extending laterally outward from the head portion; and
        a valved hub, comprising:
            a sidewall having a plurality of apertures formed therein, the plurality of apertures configured to receive the plurality of protrusions to couple the valved hub to the head portion.

9. The trocar cannula system of claim 8, wherein the hollow rod portion is fenestrated.

10. The trocar cannula system of claim 8, wherein a length of the hollow rod portion is less than or equal to four millimeters.

11. The trocar cannula system of claim 8, wherein a length of the hollow rod portion is less than or equal to two millimeters.

12. The trocar cannula system of claim 8, wherein the valved hub comprises a valve located at a central portion thereof, which is aligned with the first opening and the second opening of the hollow rod portion.

13. The trocar cannula system of claim 12, wherein the valve is configured to allow aqueous humor fluid to flow therethrough.

* * * * *